(12) United States Patent
Screen et al.

(10) Patent No.: US 8,430,854 B2
(45) Date of Patent: Apr. 30, 2013

(54) LOTION APPLICATOR AND METHOD THEREFOR

(76) Inventors: David Screen, Las Vegas, NV (US);
Kimberly Screen, Las Vegas, NV (US)

( * ) Notice: Subject to any disclaimer, the term of this patent is extended or adjusted under 35 U.S.C. 154(b) by 108 days.

(21) Appl. No.: 13/079,207

(22) Filed: Apr. 4, 2011

(65) Prior Publication Data

US 2012/0253301 A1    Oct. 4, 2012

(51) Int. Cl.
*A61M 35/00* (2006.01)
*A47K 7/02* (2006.01)

(52) U.S. Cl.
USPC ............................................ 604/310; 15/222

(58) Field of Classification Search .............. 15/222; 604/289, 290, 310
See application file for complete search history.

(56) References Cited

U.S. PATENT DOCUMENTS

| | | | | |
|---|---|---|---|---|
| 1,379,925 A | * | 5/1921 | Kawasaki | 15/222 |
| 1,488,332 A | * | 3/1924 | Foerg | 15/210.1 |
| 1,741,962 A | * | 12/1929 | Theodoropulos | 15/222 |
| 1,823,689 A | * | 9/1931 | Kelley | 15/210.1 |
| 2,008,990 A | * | 7/1935 | Mullen | 15/222 |
| 2,807,815 A | * | 10/1957 | Mack | 15/118 |
| 3,061,841 A | * | 11/1962 | Johnson | 4/615 |
| 3,720,205 A | * | 3/1973 | Liebman | 601/143 |
| 4,187,575 A | * | 2/1980 | Collins | 15/222 |
| 4,232,128 A | * | 11/1980 | Michel et al. | 521/134 |
| 4,422,205 A | * | 12/1983 | Braxter, Sr. | 15/222 |
| 4,512,054 A | * | 4/1985 | Clark | 15/222 |
| 4,672,707 A | * | 6/1987 | Johnson | 15/222 |
| 4,720,888 A | * | 1/1988 | Menz | 15/246 |
| 4,759,652 A | * | 7/1988 | Ulrich | 401/196 |
| 5,082,707 A | * | 1/1992 | Fazio | 428/43 |
| 5,251,990 A | * | 10/1993 | Vought et al. | 401/8 |
| 5,352,216 A | * | 10/1994 | Shiono et al. | 604/312 |
| 5,386,609 A | * | 2/1995 | Xenos | 15/222 |
| 5,664,281 A | * | 9/1997 | Pelfrey | 15/244.2 |
| 5,671,498 A | * | 9/1997 | Martin et al. | 15/244.3 |
| 5,736,213 A | * | 4/1998 | Meier | 428/76 |
| 5,979,006 A | * | 11/1999 | Stokes et al. | 15/222 |
| 5,983,436 A | * | 11/1999 | Mason et al. | 15/222 |
| 6,026,531 A | * | 2/2000 | Pruitt | 15/160 |
| 6,351,869 B1 | * | 3/2002 | Jones | 15/209.1 |
| 6,386,776 B2 | * | 5/2002 | Scariano | 401/8 |
| 6,656,565 B2 | * | 12/2003 | Harrison | 428/131 |
| 6,786,666 B1 | * | 9/2004 | Floyd-Williams et al. | 401/118 |
| 8,156,598 B2 | * | 4/2012 | McDowell | 15/104.94 |
| 2003/0145408 A1 | * | 8/2003 | Kohlruss et al. | 15/209.1 |
| 2006/0248672 A1 | * | 11/2006 | Dussaussoy | 15/222 |

\* cited by examiner

*Primary Examiner* — Susan Su
(74) *Attorney, Agent, or Firm* — Weiss & Moy, P.C.; Jeffrey D. Moy

(57) ABSTRACT

A device for applying lotion to a user's body has a foam layer. A cover layer is applied to a top surface of the foam layer. A pair of openings formed through the foam layer and the cover layer. A reinforcement layer is applied around each opening.

15 Claims, 1 Drawing Sheet

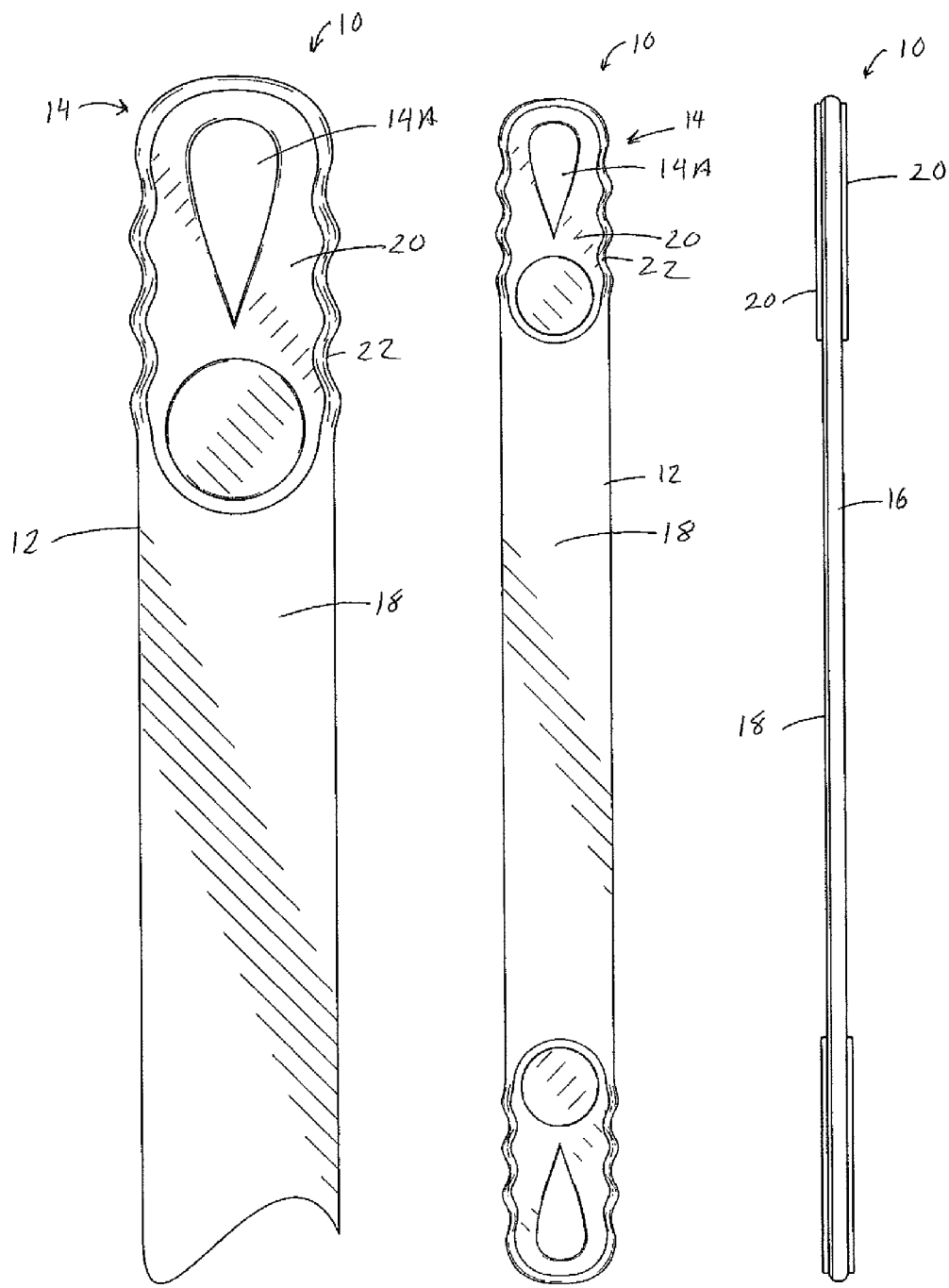

LOTION APPLICATOR AND METHOD THEREFOR

BACKGROUND

Embodiments of this disclosure relate generally to lotion applicators and, more particularly, to a lotion application that may be used to apply lotion to a user's back.

Presently, there are many different types of devices which may enable a person to apply a cleaner, such as soap, or a lotion to an area of the body. More specifically, most of these types of devices may be used to apply the soap and or lotion to areas of the person's body that may be difficult to access with one's hands or a hand-held wash cloth.

One type of applicator is a handle and brush/sponge combination. The problem with this type of device is that the brush/sponge area is relatively small. Thus, it may be difficult to ensure that all areas of the user's back have been reached. Further, these type of devices have handles which are of fixed length. This can lead to difficulty in efficiently using a fixed length applicator by person's of different size who must grasp the ends of the applicator and try to manipulate it behind their back.

Other types of applicator devices may be characterized as having an elongated flexible strip of fabric material where soap and or lotion may be applied. Hand grippable handles, frequently formed by fabric loops or the like, enable the user to grasp opposite ends of the applicator and extend it across his/her back in a manipulating movement. Unfortunately, if the strip of fabric is too flexible, the soap/lotion may not be properly applied as the soap/lotion may not be evenly applied. Similarly, if the strip of fabric is too stiff, the soap/lotion will not be properly applied as areas of the user's back may not be reached since the strip of fabric may not be able to bend to reach all areas of the user's back.

Therefore, it would be desirable to provide a system and method that overcomes the above

SUMMARY

A device for applying lotion to a user's body has a foam layer. A cover layer is applied to a top surface of the foam layer. A pair of openings formed through the foam layer and the cover layer. A reinforcement layer is applied around each opening.

A device for applying lotion to a user's body has a strip member. The strip member comprises a foam layer and a cover layer applied to a top surface of the foam layer. An opening is formed through each end of the strip member through the foam layer and the cover layer. A reinforcement layer is applied to a top surface of the cover layer around each opening and to a bottom surface of the foam layer around each opening.

The features, functions, and advantages can be achieved independently in various embodiments of the disclosure or may be combined in yet other embodiments.

BRIEF DESCRIPTION OF THE DRAWINGS

Embodiments of the disclosure will become more fully understood from the detailed description and the accompanying drawings, wherein:

FIG. 1 is a magnified view of the handle area of the applicator of the present invention;

FIG. 2 is a top view of the applicator of the present invention; and

FIG. 3 is a side view of the applicator of the present invention.

DETAILED DESCRIPTION

Referring to FIGS. 1-3, an applicator 10 is shown. The applicator 10 may be used to apply soap, lotion or the like (hereinafter lotion) to areas of a user's body which may be hard to reach. In accordance with one embodiment, the applicator 10 may be used to apply lotion to the back of a user.

The applicator 10 may be comprised of body member 12. The body member 12 may have handle members 14 formed on each end of the body member 12. The body member 12 is formed of a material that is flexible to evenly apply the lotion to the user, but stiff enough to evenly apply the lotion.

In accordance with one embodiment, the body member 12 may be formed of a foam layer 16. The foam layer 16 may allow the body member 12 to be flexible so that the body member 12 conforms to the shape of the user. This may allow the applicator 10 to more easily reach all areas of the user's body. In accordance with one embodiment, the foam layer 16 may be formed of Ethylene vinyl acetate (EVA) foam. EVA foam is a closed cell foam that is weather and chemical resistant; has low water absorption; oil resistant; and is environmentally friendly that allows for safe disposal by recycling, dumping or incineration. EVA foam is a dense foam that readily accepts paint, glues and various finishes.

A cover layer 18 may be applied to one or more of the surfaces of the foam layer 16. The cover layer 18 may have similar characteristic as the foam layer 16 such as being weather and chemical resistant; water resistant; oil resistant; and the like. The cover layer 18 may be formed of a material such as a water resistant leather, vinyl, or the like. The listing of the above is given as an example and should not be seen in a limiting manner. In accordance with one embodiment, the cover layer 18 may be textured. By having a textured surface on the cover layer 18, one may gentle massage and/or exfoliate the area where the lotion is being applied.

On each end of the body member 12 may be a handle 14. In accordance with one embodiment, the handle 14 may be formed by forming an opening 14A in each end of the body member 12. The opening 14A may be oval in shape to allow the opening 14A to conform to the shape of the user's hands which may be slid through the openings 14A to grab the applicator 10.

A reinforcement layer 20 may be applied on a top and/or bottom section of the opening 14A. In the embodiment shown in the Figures, the reinforcement layer 20 may be applied to the cover layer 18 around the opening 14A. The reinforcement layer 20 may be applied to bottom side of the foam layer 16 around the opening 14A. The reinforcement layer 20 may be used to prevent the opening 14A from tearing. The reinforcement layer 20 may be formed of similar material as the cover layer 18. In accordance with one embodiment, the reinforcement layer 20 may be formed thicker than the cover layer 18 to provide further reinforcement.

In accordance with one embodiment, a plurality of indentations 22 may be formed around the outer perimeter of each opening 14A. The indentations 22 may be used as grip members when a user's hands are inserted through each opening 14A.

While embodiments of the disclosure have been described in terms of various specific embodiments, those skilled in the art will recognize that the embodiments of the disclosure can be practiced with modifications within the spirit and scope of the claims.

What is claimed is:

1. A device for applying lotion to a user's body comprising:
   a strip member comprising:
   a foam layer; and
   a textured cover layer applied to only a top surface of the foam layer such that a bottom surface of the foam layer can directly contact the user's body;
   an opening formed through each end of the strip member through the foam layer and the cover layer;
   a plurality of indentations formed on each of two peripheral edges of the strip member around the opening formed through each end of the strip member, wherein the indentations form a gripping area; and
   a reinforcement layer applied to a top surface of the cover layer around each opening and to a bottom surface of the foam layer around each opening.

2. A device for applying lotion to a user's body in accordance with claim 1, wherein the foam layer is an ethylene vinyl acetate (EVA) foam layer.

3. A device for applying lotion to a user's body in accordance with claim 1, wherein the cover layer is leather.

4. A device for applying lotion to a user's body comprising:
   a strip member comprising:
   a foam layer; and
   a textured cover layer applied to only a top surface of the foam layer such that a bottom surface of the foam layer can directly contact the user's body;
   an opening formed through each end of the strip member through the foam layer and the cover layer;
   a plurality of indentations formed on each of two peripheral edges of the strip member around the opening formed through each end of the strip member, wherein the indentations form a gripping area; and
   a reinforcement later applied around each opening.

5. A device for applying lotion to a user's body in accordance with claim 4, wherein the reinforcement layer is applied to a top surface of the cover layer around each opening.

6. A device for applying lotion to a user's body in accordance with claim 4, wherein the reinforcement layer is applied to a bottom surface of the foam layer around each opening.

7. A device for applying lotion to a user's body in accordance with claim 4, wherein the reinforcement layer is applied to a top surface of the cover layer around each opening and to a bottom surface of the foam layer around each opening.

8. A device for applying lotion to a user's body in accordance with claim 4, wherein the foam layer is an ethylene vinyl acetate (EVA) foam layer.

9. A device for applying lotion to a user's body in accordance with claim 4, wherein the cover layer is leather.

10. A device for applying lotion to a user's body consisting of:
    a foam layer;
    a textured cover layer applied to only a top surface of the foam layer such that a bottom surface of the foam layer can directly contact the user's body;
    a pair of openings formed through the foam layer and the cover layer;
    a plurality of indentations formed on each of two peripheral edges of the device around each opening, wherein the indentations form a gripping area; and
    a reinforcement layer applied around each opening.

11. A device for applying lotion to a user's body in accordance with claim 10, wherein the reinforcement layer is applied to a top surface of the cover layer around each opening.

12. A device for applying lotion to a user's body in accordance with claim 10, wherein the reinforcement layer is applied to the bottom surface of the foam layer around each opening.

13. A device for applying lotion to a user's body in accordance with claim 10, wherein the reinforcement layer is applied to a top surface of the cover layer around each opening and to bottom surface of the foam layer around each opening.

14. A device for applying lotion to a user's body in accordance with claim 10, wherein the foam layer is an ethylene vinyl acetate (EVA) foam layer.

15. A device for applying lotion to a user's body in accordance with claim 10, wherein the cover layer is leather.

* * * * *